United States Patent
Shih

(10) Patent No.: US 10,126,240 B2
(45) Date of Patent: Nov. 13, 2018

(54) BIOLOGICAL DETECTION CALIBRATION SYSTEM

(71) Applicant: Wistron Corporation, New Taipei (TW)

(72) Inventor: Wen-Hui Shih, New Taipei (TW)

(73) Assignee: Wistron Corporation, New Taipei (TW)

( * ) Notice: Subject to any disclaimer, the term of this patent is extended or adjusted under 35 U.S.C. 154(b) by 0 days.

(21) Appl. No.: 15/052,890

(22) Filed: Feb. 25, 2016

(65) Prior Publication Data
US 2016/0169803 A1 Jun. 16, 2016

Related U.S. Application Data

(62) Division of application No. 13/902,865, filed on May 27, 2013.

(30) Foreign Application Priority Data

Aug. 17, 2012 (TW) .............................. 101129897 A

(51) Int. Cl.
*G01N 21/00* (2006.01)
*G01N 21/01* (2006.01)
(Continued)

(52) U.S. Cl.
CPC ......... *G01N 21/6428* (2013.01); *G01D 18/00* (2013.01); *G01N 21/274* (2013.01); *G01N 21/6452* (2013.01); *G01N 21/6458* (2013.01); *G01N 21/6486* (2013.01); *G02B 21/0096* (2013.01); *G02B 21/06* (2013.01); *G02B 21/16* (2013.01); *G02B 21/365* (2013.01);
(Continued)

(58) Field of Classification Search
CPC ............ A61B 5/14532; A61B 5/14558; G01D 18/00; G01N 21/274; G01N 21/6452; G01N 21/6486
USPC ..... 422/82.05, 401, 407, 408, 63, 68.1, 560, 422/561
See application file for complete search history.

(56) References Cited

U.S. PATENT DOCUMENTS

| | | | |
|---|---|---|---|
| 5,192,980 A * | 3/1993 | Dixon | G01J 3/30 250/458.1 |
| 2003/0049865 A1* | 3/2003 | Santini, Jr. | A61B 5/00 436/518 |

(Continued)

*Primary Examiner* — Dean Kwak
(74) *Attorney, Agent, or Firm* — JCIPRNET

(57) ABSTRACT

A biological detection calibration system includes a biological detection device and a light calibration device. The biological detection device is for detecting a biological sample and includes a light source and a controller electrically connected thereto to control the light source to emit a light. The light calibration device includes a carrier, disposed at a detecting position of the biological sample in the biological detection device to receive the light emitted from the light source, and a calibration sample, disposed on the carrier and including a light detector. The light detector is for detecting intensity of the light and transmitting intensity information to the controller. The controller reads the intensity information of the light and compares the intensity information with a predetermined value to modify driving energy of the light source so that the intensity of the light detected by the light detector is not less than the predetermined value.

10 Claims, 4 Drawing Sheets

(51) Int. Cl.
*G01N 21/64* (2006.01)
*G01D 18/00* (2006.01)
*G01N 21/27* (2006.01)
*G02B 21/00* (2006.01)
*G02B 21/06* (2006.01)
*G02B 21/16* (2006.01)
*G02B 21/36* (2006.01)

(52) U.S. Cl.
CPC . *G01N 2201/061* (2013.01); *G01N 2201/062* (2013.01); *G01N 2201/127* (2013.01)

(56) References Cited

U.S. PATENT DOCUMENTS

2006/0141611 A1* 6/2006 Frutos ............... G01N 21/253
435/287.2
2007/0211245 A1* 9/2007 Pastel ............... B01L 3/5085
356/246

* cited by examiner

BIOLOGICAL DETECTION CALIBRATION SYSTEM

CROSS-REFERENCE TO RELATED APPLICATION

This application is a divisional application of U.S. application Ser. No. 13/902,865, filed on May 27, 2013, now pending. The prior application Ser. No. 13/902,865 claims the priority benefit of Taiwan application serial no. 101129897, filed on Aug. 17, 2012. The entirety of each of the above-mentioned patent application is hereby incorporated by reference herein and made a part of this specification.

BACKGROUND OF THE INVENTION

Field of the Invention

The invention relates to a light calibration device, a biological detection calibration system, and an operating method thereof, and particularly relates to a light calibration device, a biological detection calibration system, and an operating method thereof that are developed for a biological detection device emitting a light with certain intensity and wavelength to a biological sample to detect a fluorescence thereof.

Description of Related Art

Now, in the field of biological detection, fluorescence detection technology is often used for detecting whether a biological sample shows a positive or negative reaction. In the process of generating a fluorescence, an additional light source is usually required to be used as an excitation light source. The problem of luminous decay may occur on the light source (whether mercury lamps or LEDs) after the light source is used for a long period of time. When such a problem occurs, a light calibration device is needed to calibrate the light source. Through adjusting the intensity of the light source, erroneous detection results due to insufficient fluorescence resulting from luminous decay are prevented.

However, most light sources are integrated into the biological detection devices, and the designs of the light sources may vary according to different biological detection devices. The light sources in different biological detection devices may not have fixed size, shape, or position. Thus, a method for taking out the light sources and effectively measuring the intensity thereof may differ according to different biological detection devices, which relatively increases the difficulty in light source calibration. Moreover, in order to perform light source calibration, it is usually required to purchase an expensive and heavy light source calibration device, disassemble the light source, and install the light source calibration device for calibration process. Such a calibration process is complex and requires much work, and the equipment costs are high, which are unfavorable for the development of light-weighted portable biological detection devices.

SUMMARY OF THE INVENTION

The invention provides a light calibration device for measuring an intensity of a light source of a biological detection device in a simplified way.

The invention provides a biological detection calibration system, wherein a light detector is integrated with a carrier for biochemical examination for directly measuring the intensity of the light source of the biological detection device on the carrier, and the intensity of the light source is compensated by a controller of the biological detection device. The light source of the biological detection device does not need to be taken out during a calibration process, and thus the calibration of the light source is greatly simplified.

The invention provides an operating method of the biological detection calibration system.

The invention provides a light calibration device adapted for a biological detection device for detecting a biological sample, wherein the biological detection device includes a light source and a controller, and the light calibration device includes a carrier and a calibration sample. The carrier is disposed at a detecting position of the biological sample in the biological detection device for receiving a light emitted from the light source. The calibration sample is disposed on the carrier and includes a light detector. The light detector is adapted for detecting the intensity of the light emitted from the light source to the carrier, and the calibration sample is adapted for transmitting intensity information of the light detected by the light detector to the controller.

In an embodiment of the invention, the carrier is a blank micro titer plate and includes at least one recess, wherein the light detector is disposed at a position corresponding to the at least one recess.

The invention further provides a biological detection calibration system that includes a biological detection device and a light calibration device. The biological detection device is used for detecting a biological sample and includes a light source and a controller. The light source emits a light to the biological sample. The controller is electrically connected to the light source to drive and control the light source to emit the light. The light calibration device includes a carrier and a calibration sample, wherein the carrier is disposed at a detecting position of the biological sample in the biological detection device to receive the light emitted from the light source. The calibration sample is disposed on the carrier and includes a light detector. The light detector is adapted for detecting the intensity of the light emitted to the carrier and transmitting intensity information to the controller. The controller is adapted for reading the intensity information of the light detected by the light detector and comparing the intensity information with a predetermined value to adjust driving energy of the light source, so that the intensity of the light detected by the light detector is not less than the predetermined value.

The invention further provides an operating method of a biological detection calibration system, adapted for a biological detection device which includes a light source for emitting a light to detect a biological sample. The operating method includes the following steps. A step is performed to detect whether a light calibration device exists on the biological detection device, wherein the light calibration device includes a carrier and a calibration sample disposed on the carrier, and the calibration sample includes a light detector. If the light calibration device exists, the intensity of the light detected by the light detector is read to determine whether the intensity of the light detected by the light detector is less than a predetermined value. If the intensity of the light detected by the light detector is less than the predetermined value, a driving voltage of the light source is enhanced, such that the intensity of the light detected by the light detector reaches the predetermined value.

Based on the above, although different biological detection devices may adopt light sources with different designs, the lights of the light sources of the biological detection devices are all emitted to the carrier for biochemical examination. Considering this characteristic, the light calibration device and the biological detection calibration system of the invention integrate the light detector with the carrier for directly measuring the intensity of the light source of the biological detection device on the carrier, so as to detect the light intensity that the biological sample receives during actual examination. Moreover, the controller compares the intensity information of the light detected by the light detector with the predetermined value to adjust the intensity of the light source. Therefore, the light calibration device, the biological detection calibration system, and the operating method of the invention can be used to calibrate the light source of the biological detection device without disassembling the light source, which is very convenient in operation.

To make the aforementioned and other features and advantages of the invention more comprehensible, several embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1A:
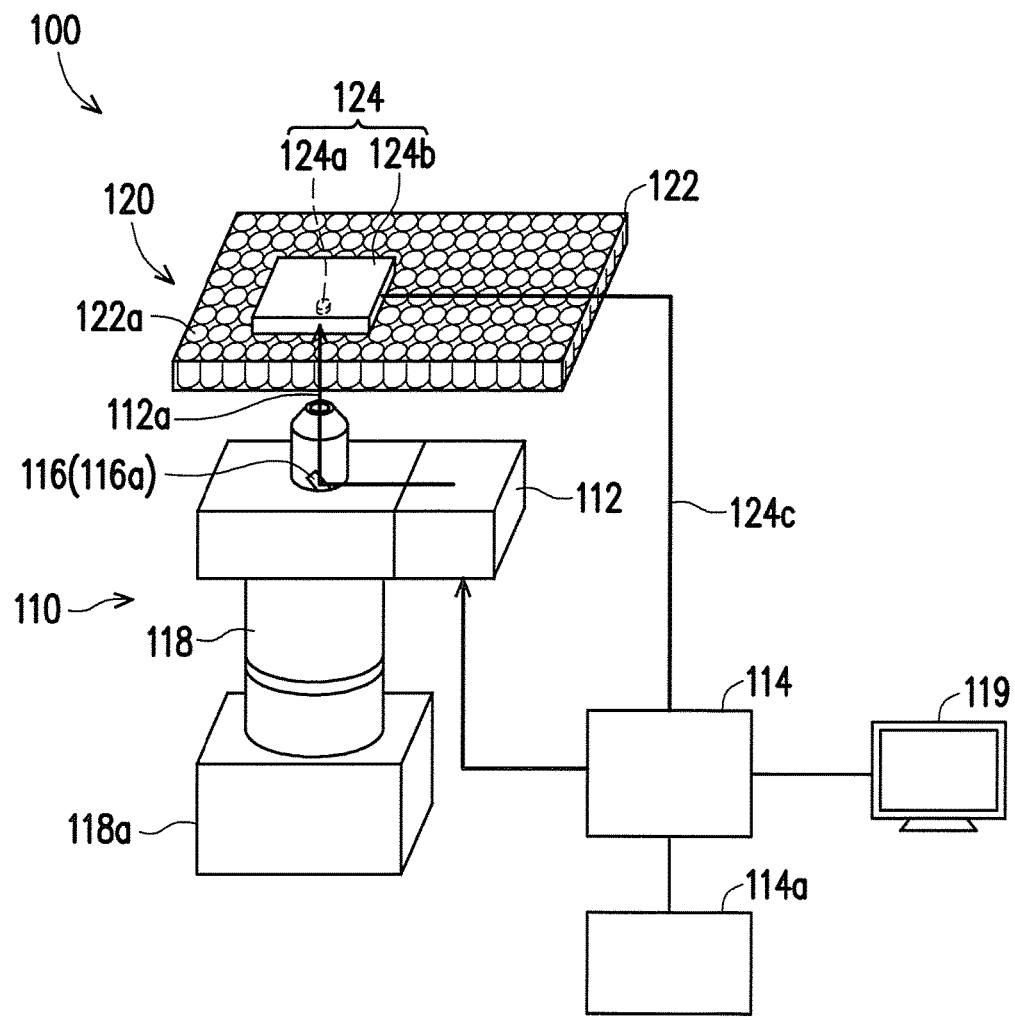
FIG. 1A is a schematic view of a biological detection calibration system according to an embodiment of the invention.
Figure 1B:
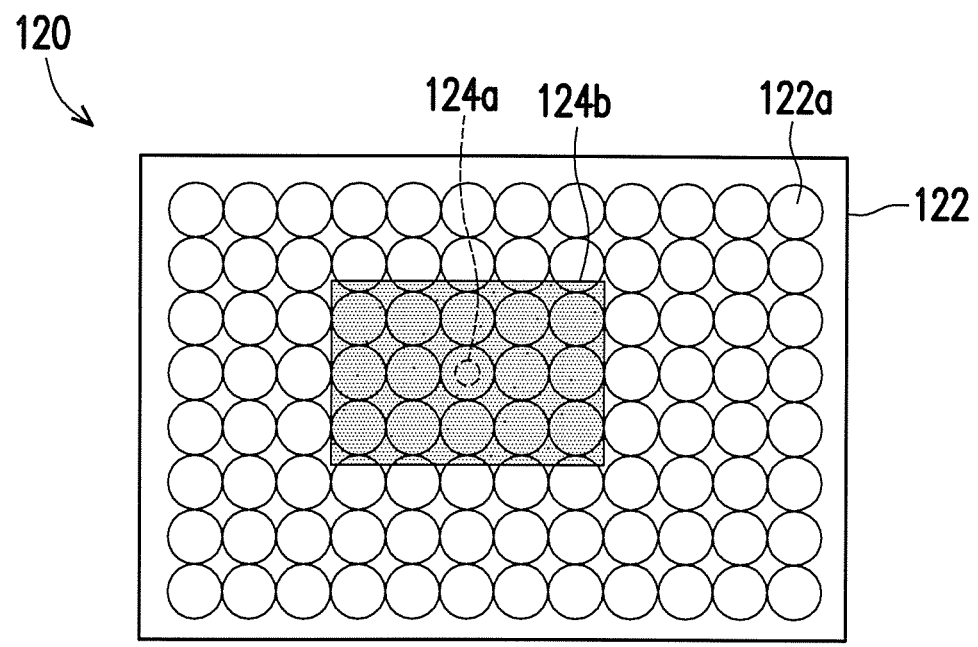
FIG. 1B is a schematic top view of a light calibration device of the biological detection calibration system in FIG. 1A.
Figure 1C:
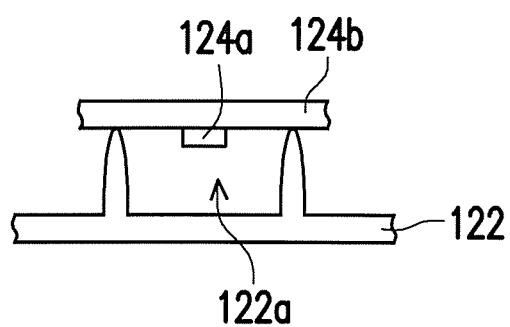
FIG. 1C is a schematic cross-sectional view illustrating a part of the light calibration device of the biological detection calibration system in FIG. 1B.

FIG. 1A is a schematic view of a biological detection calibration system according to an embodiment of the invention. FIG. 1B is a schematic top view of a light calibration device of the biological detection calibration system in FIG. 1A. FIG. 1C is a schematic cross-sectional view illustrating a part of the light calibration device of the biological detection calibration system in FIG. 1B.

Referring to FIG. 1A to FIG. 1C, a biological detection calibration system 100 of this embodiment includes a biological detection device 110 and a light calibration device 120. The biological detection device 110 includes a light source 112 and a controller 114. In this embodiment, the biological detection device 110 is a fluorescence micrography detecting device, but it is noted that the biological detection device 110 is not limited thereto. The controller 114 is electrically connected to the light source 112 and applies a constant driving voltage, so as to control the light source 112 to emit a light 112a having a predetermined intensity and a wavelength within a specific range.

The light calibration device 120 includes a carrier 122 and a calibration sample 124 disposed on the carrier 122. In this embodiment, the carrier 122 may be a blank 96-well micro titer plate. That is to say, the same as a general (96-well) micro titer plate, the carrier 122 also includes a plurality of (96) recesses 122a, but it is noted that the carrier 122 is not limited to the above. The calibration sample 124 includes a light detector 124a. The light detector 124a is disposed in one of the recesses 122a of the carrier 122.

Generally speaking, a biological sample that is to be detected by the fluorescence micrography detecting device is placed in the recess of the micro titer plate. Because a path of the light emitted by the light source of the fluorescence micrography detecting device passes through the recess, the biological sample is irradiated by the light to generate a fluorescence. In this embodiment, a 96-well micro titer plate, the same as that for performing fluorescence detection, is used as the carrier 122 of the light calibration device 120. Moreover, a position of the carrier 122 relative to the biological detection device 110 is identical to a position of the 96-well micro titer plate relative to the fluorescence micrography detecting device when detection is carried out. In other words, the light detector 124a is located on the path of the light 112a. Therefore, during a calibration process, the light detector 124a is able to detect the intensity of the light that is emitted on the biological sample from the biological detection device 110. That is to say, the carrier 122 in which the light detector 124a is disposed is used to simulate a situation of performing detection on the 96-well micro titer plate that actually has the biological sample thereon.

In this embodiment, the calibration sample 124 further includes a circuit board 124b, which is electrically connected to the light detector 124a and the controller 114. As shown in FIG. 1A and FIG. 1C, the circuit board 124b may be disposed on the carrier 122 in a way that the light detector 124a faces downward to receive the light 112a. However, in another embodiment, if the circuit board 124b is designed to have a smaller size, the circuit board 124b may also be disposed in one of the recesses 122a of the carrier 122. Intensity information of the light 112a detected by the light detector 124a is converted from a voltage to a digital signal via the circuit board 124b and transmitted to the controller 114 by a wired means, i.e. via a transmission line 124c. Of course, the intensity information of the light 112a detected by the light detector 124a may also be transmitted to the controller 114 by other means, e.g. via wireless communication.

After reading the digital signal indicating the intensity information of the light 112a detected by the light detector 124a, the controller 114 compares the digital signal with an initial intensity of the light source 112 or an intensity of a standard work state of the light source 112 (i.e. a predetermined value). If the intensity of the light 112a detected by the light detector 124a is the same as the predetermined value, it indicates that the intensity of the light 112a is sufficient for the biological sample to generate a proper fluorescence, which means that the light source 112 does not have the problem of luminous decay, and thus the driving voltage of the light source 112 does not need to be adjusted. However, if the intensity of the light 112a detected by the light detector 124a is different from the predetermined value, it indicates that the light source 112 may have the problem of luminous decay. In order to prevent the biological detection device 110 from generating incorrect detection results due to insufficient fluorescence which results from luminous decay when performing fluorescence detection on the biological sample, the biological detection calibration system 100 of this embodiment utilizes the controller 114 to adjust the driving voltage of the light source 112, for example by enhancing the driving voltage of the light source 112 such that the intensity of the light 112a detected by the light detector 124a reaches the predetermined value.

In this embodiment, the biological detection device 110 further includes an optical device 116, a microscope module 118, an image capturing module 118a, a control interface 114a, and a display module 119. The optical device 116 is used for guiding the light 112a of the light source 112 along a direction toward the carrier 122 of the invention or the general 96-well micro titer plate. As shown in FIG. 1A, in this embodiment, the optical device 116 is a mirror, which reflects the light 112a emitted by the light source 112 to a direction toward the light detector 124a, but it is noted that the optical device 116 is not limited to the above.

Generally, when the biological detection device 110 is used to perform fluorescence examination, the 96-well micro titer plate having the biological sample thereon is placed at the position of the light calibration device 120, as shown in FIG. 1A, and the light 112a emitted from the light source 112 of the biological detection device 110 is reflected by the optical device 116 to the biological sample to generate fluorescence. As illustrated in FIG. 1A, the microscope module 118 is disposed at a side of the optical device 116 opposite to the 96-well micro titer plate for receiving the fluorescence of the biological sample, and the image capturing module 118a is used to capture an image of the fluorescence.

In addition, the control interface 114a is electrically connected to the controller 114 for the user to perform various function operations or parameter settings on the controller 114, and the control interface 114a may be an input device, e.g. button, keyboard, switch, or touch screen. The display module 119 is electrically connected to the controller 114 for displaying the intensity information of the light 112a received by the controller 114 or a comparison result. In this embodiment, the display module 119 is a screen, which may be an independent screen or a screen of a computer device. However, in other embodiments, the display module 119 may be a lamp which shows the comparison result by turning on/off or blinking of the lamp. Of course, the display module 119 is not limited to the above, and the control interface 114a, the controller 114, and the display module 119 may be integrated as one single device.

Figure 2:
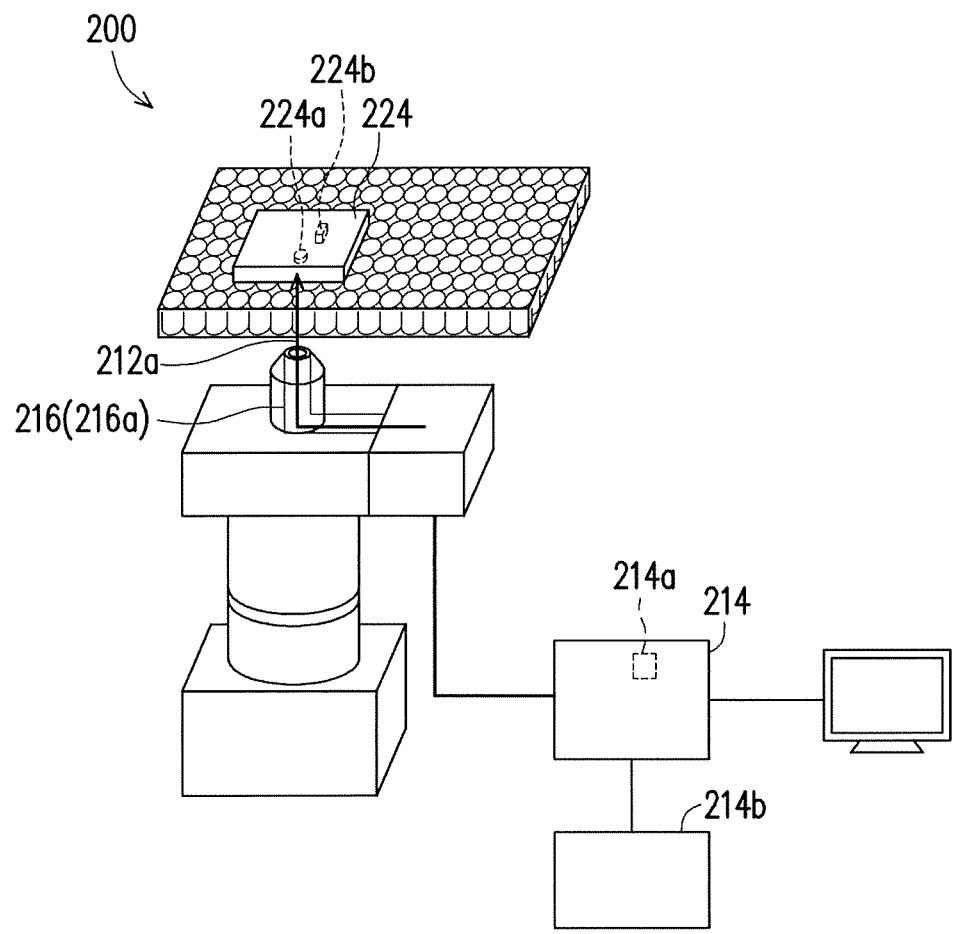
FIG. 2 is a schematic view of a biological detection calibration system according to another embodiment of the invention.

FIG. 2 is a schematic view of a biological detection calibration system according to another embodiment of the invention. Referring to FIG. 2, a main difference between a biological detection calibration system 200 of FIG. 2 and the biological detection calibration system 100 of FIG. 1A lies in that: a calibration sample 224 of the biological detection calibration system 200 of FIG. 2 further includes a wireless transmission unit 224b, and a controller 214 includes a wireless reception unit 214a and a control interface 214b.

The control interface 214b is electrically connected to the controller 214 for the user to perform various function operations or parameter settings on the controller 214, and the control interface 214b may be an input device, e.g. button, keyboard, switch, or touch screen. In this embodiment, intensity information of a light 212a detected by a light detector 224a is transmitted from the wireless transmission unit 224b to the wireless reception unit 214a of the controller 214 by a wireless means. Of course, the intensity information of the light 212a detected by the light detector 224a may also be transmitted to the controller 214 by other means, which is not limited to the above.

Moreover, in comparison with FIG. 1A in which the optical device 116 is the mirror 116a, an optical device 216 of this embodiment is an optical fiber 216a. The biological detection device 200 of FIG. 2 guides the light 212a to the light detector 214a via the optical fiber 216a.

Figure 3:
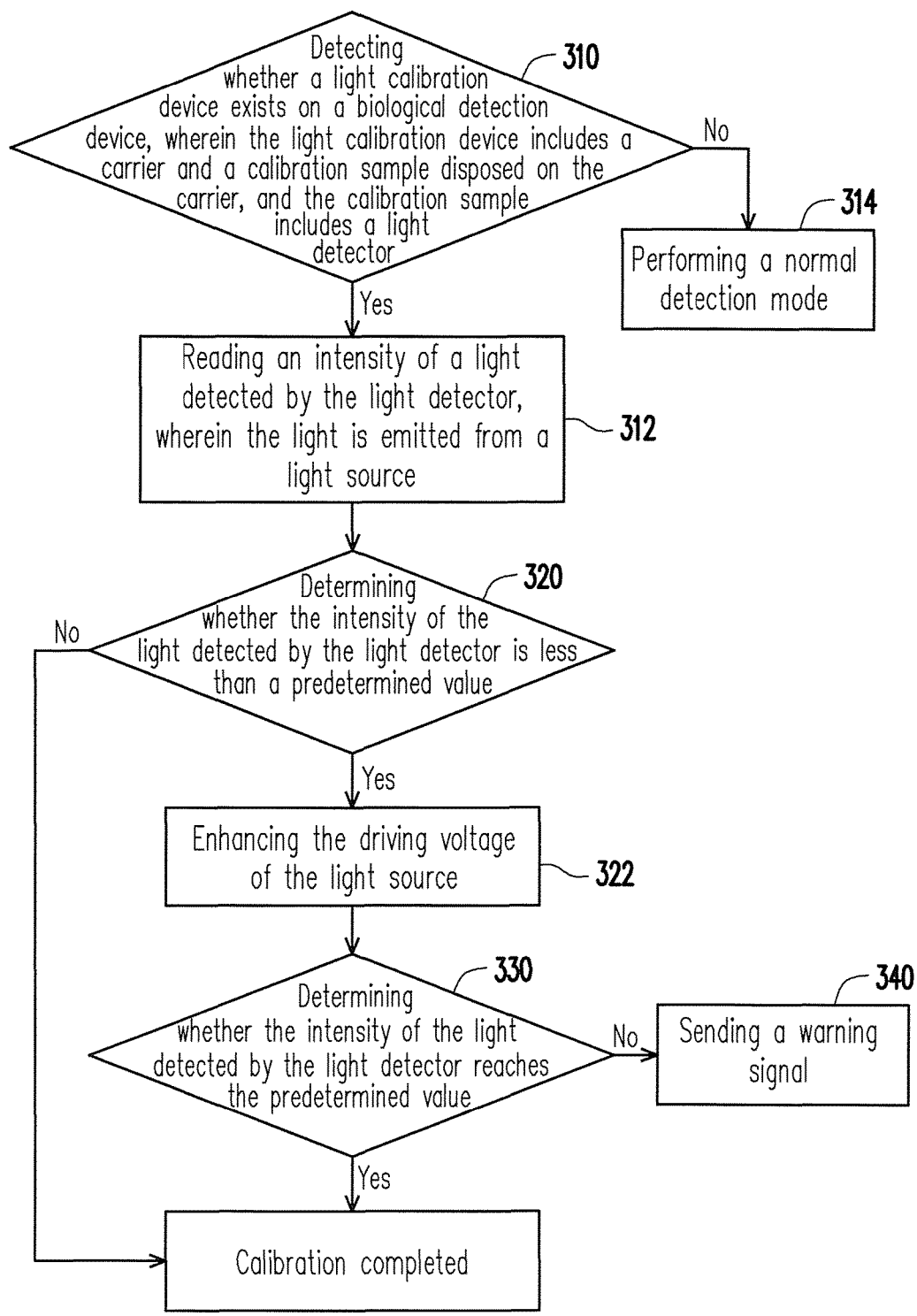
FIG. 3 is a flowchart showing an operating method of a biological detection calibration system according to an embodiment of the invention.

FIG. 3 is a flowchart showing an operating method of a biological detection calibration system according to an embodiment of the invention. Referring to FIG. 3, the operating method of the biological detection calibration system of this embodiment is adapted for a biological detection device which includes a light source for emitting a light to detect a biological sample. The operating method includes the following steps: first, detecting whether a light calibration device is on the biological detection device, wherein the light calibration device includes a carrier and a calibration sample disposed in the carrier, and the calibration sample includes a light detector (Step 310). If the light calibration device exists, an intensity of the light detected by the light detector is read, wherein the light is emitted from a light source (Step 312). If the light calibration device does not exist, a normal detection mode is performed (Step 314).

In this embodiment, the carrier is a micro titer plate and includes a plurality of recesses. The light detector is disposed in one of the recesses. The biological detection device includes a controller adapted for driving and controlling the light source to emit the light. Step 310 is to detect whether the light detector sends a signal indicating detection of the light via the controller, so as to determine whether to perform an operating process of the biological detection calibration system.

Thereafter, if the light calibration device exists, a step is performed to determine whether the intensity of the light detected by the light detector is less than a predetermined value (Step 320). If the intensity of the light detected by the light detector is less than the predetermined value, the driving voltage of the light source is enhanced (Step 322). If the intensity of the light detected by the light detector is not less than the predetermined value, the calibration is completed.

The light detector is located on the path of the light. The light detector detects the intensity of the light and transmits the detection results to the controller by wired means (e.g. the light detector is connected to the controller via a circuit board and a transmission line) or wireless means (e.g. the calibration sample includes a wireless transmission unit and the controller includes a wireless reception unit, and the intensity information of the light detected by the light detector is transmitted to the wireless reception unit of the controller via the wireless transmission unit), so as to allow the controller to read the intensity of the light detected by the light detector.

After enhancing the driving voltage of the light source, a step is performed to determine whether the intensity of the light detected by the light detector reaches the predetermined value (Step 330).

The controller compares the intensity of the light detected by the light detector with the predetermined value. Specifically, in this embodiment, the controller compares the intensity of the light detected by the light detector and read by the controller with an intensity value of the light (i.e. the predetermined value) that the light source is initially controlled to emit, so as to determine whether the intensity of the light that the light source is expected to emit is the same as the intensity of the light detected by the light detector. If the two intensities are the same, it indicates that the intensity of the light emitted by the light source does not decay, and thus there is no need to adjust the intensity of the light source. If the two intensities are different, it indicates that the intensity of the light emitted by the light source may have decayed. Insufficient intensity of the light may result in low fluorescence. Hence, the driving voltage of the light source is enhanced, so as to raise the intensity of the light detected by the light detector up to the predetermined value. After the driving voltage of the light source is enhanced, the controller again determines whether the intensity of the light detected by the light detector reaches the predetermined value.

If the intensity of the light detected by the light detector reaches the predetermined value after the driving voltage of the light source is enhanced, the calibration is completed. If the intensity of the light detected by the light detector is still less than the predetermined value after the driving voltage of the light source is enhanced, a warning signal is sent (Step 340). In this embodiment, the biological detection device further includes a display module electrically connected to the controller. The controller transmits the warning signal to the display module, wherein the display module is a screen, which may be an independent screen or a screen of a computer device. However, in other embodiments, the display module may be a lamp which shows the comparison result by turning on/off or blinking of the lamp. Of course, the display module is not limited to the above. The above-disclosed operating method of the biological detection calibration system effectively calibrates the intensity of the light source of the biological detection device and prevents erroneous detection results due to low fluorescence which results from insufficient intensity of the light source of the biological detection device.

In conclusion of the above, although different biological detection devices may adopt light sources with different designs, the lights of the light sources of the biological detection devices are all emitted to the recesses of the micro titer plate for biochemical examination. In view of this characteristic, the light calibration device and the biological detection calibration system of the invention integrate the light detector with the carrier for directly measuring the intensity of the light source of the biological detection device on the carrier, so as to detect the light intensity that the biological sample receives during actual examination. Furthermore, the controller compares the intensity information of the light detected by the light detector with the predetermined value to adjust the actual intensity of the light source to the predetermined value, so as to overcome the problem of luminous decay. According to the invention, the light calibration device, the biological detection calibration system, and the operating method of the invention can be used to directly calibrate the light source of the biological detection device without disassembling the light source, which is very convenient in operation. Since it is not required to purchase an expensive and heavy light source calibration device, the costs are saved.

It will be apparent to those skilled in the art that various modifications and variations can be made to the disclosed embodiments without departing from the scope or spirit of the invention. In view of the foregoing, it is intended that the invention covers modifications and variations of this disclosure provided that they fall within the scope of the following claims and their equivalents.

What is claimed is:

1. A biological detection calibration system, comprising:
　a biological detection device configured to detect a biological sample and comprising:
　　a titer plate comprising a light source configured to emit a light to the biological sample that is to be detected;
　　an image capturing module configured to capture a fluorescence of the biological sample generated when irradiated by the light; and
　　a controller electrically connected to the light source and configured to drive and control the light source to emit the light, and the controller electrically connected to the image capturing module and configured to detect the biological sample;
　a light calibration device, comprising:
　　a carrier configured to substitute the titer plate and disposed at a detecting position same as where the titer plate being disposed in the biological detection device to receive the light emitted from the light source to simulate the detection of the biological sample, and the carrier including a plurality of recesses;
　　a calibration sample disposed on the carrier, the calibration sample separated and independent from the light source; the calibration sample comprises a circuit board and a light detector, the circuit board electrically connected to the light detector and the controller, the light detector disposed in a position corresponding to at least one of the recesses of the carrier and configured to detect the intensity of the light directly emitted from the light source to the carrier, the light detector located on an emitting path of the light, and the calibration sample transmitting an intensity signal of the light detected by the light detector to the controller; wherein the circuit board is disposed on the carrier and the light detector is disposed to face the at least one recess to detect the intensity of the light emitted from the light source to the recess; and
　　wherein the controller is configured to operate in a calibration mode when the carrier carrying the calibration sample substitutes the titer plate to control the light source to emit the light to the calibration sample, receive the intensity signal of the light detected by the light detector, compare the intensity signal with a predetermined value, and control the light source by adjusting driving energy of the light source to increase the intensity if the intensity signal detected is less than the predetermined value.

2. The biological detection calibration system according to claim 1, wherein the carrier is a blank titer plate.

3. The biological detection calibration system according to claim 1, wherein the circuit board further comprises a wireless transmission unit and correspondingly the controller comprises a wireless reception unit, and the light detector is configured to transmit the intensity signal of the light detected by the light detector to the wireless reception unit of the controller via the wireless transmission unit.

4. The biological detection calibration system according to claim 1, wherein the circuit board together with the light detector is disposed in the at least one recess of the carrier.

5. The biological detection calibration system according to claim 1, wherein the biological detection device further comprises an optical device guiding the light of the light source to a position to irradiate the carrier.

6. The biological detection calibration system according to claim 5, wherein the optical device is a mirror or an optical fiber.

7. The biological detection calibration system according to claim 6, wherein the biological detection device further comprises a microscope module, wherein the microscope module is disposed at a side of the optical device opposite to the carrier configured to receive the fluorescence of the biological sample to which the light is emitted, and the image capturing module captures an image of the fluorescence.

8. The biological detection calibration system according to claim 1, wherein the biological detection device further comprises a display module electrically connected to the controller.

9. The biological detection calibration system according to claim 1, wherein the biological detection device further comprises a control interface electrically connected to the controller configured to perform a function operation or parameter setting on the controller.

10. The biological detection calibration system according to claim 1, wherein the controller transmits a warning signal to a warning device to notify a user if the intensity detected is still less than the predetermined value after the intensity has increased.

* * * * *